United States Patent [19]

Komatsu et al.

[11] Patent Number: 5,430,786
[45] Date of Patent: Jul. 4, 1995

[54] ELEMENT ANALYZING METHOD

[75] Inventors: Fumio Komatsu, Fuchu; Kunihiro Miyazaki, Tokyo; Ayako Shimazaki, Yokohama, all of Japan

[73] Assignee: Kabushiki Kaisha Toshiba, Kawasaki, Japan

[21] Appl. No.: 161,270

[22] Filed: Dec. 3, 1993

[30] Foreign Application Priority Data

Dec. 4, 1992 [JP] Japan ................. 4-325655

[51] Int. Cl.⁶ .............................. G01N 23/223
[52] U.S. Cl. .............................. 378/45; 364/498
[58] Field of Search ............. 378/44, 45; 364/497, 364/498

[56] References Cited

U.S. PATENT DOCUMENTS

| | | |
|---|---|---|
| 4,974,209 | 11/1990 | Hoult ...................... 364/497 |
| 5,249,216 | 9/1993 | Ohsungi et al. ............ 378/46 |
| 5,369,275 | 11/1994 | Usui et al. ................ 250/310 |

FOREIGN PATENT DOCUMENTS

4131751 5/1992 Japan ..................... 378/44

*Primary Examiner*—Paul M. Dzierzynski
*Assistant Examiner*—David Vernon Bruce
*Attorney, Agent, or Firm*—Oblon, Spivak, McClelland, Maier, & Neustadt

[57] ABSTRACT

Element identification and concentration calculation can be conducted with precision by correcting waveform distortion caused by the energy resolution of a detection system. A smoothing process is effected on a measured waveform of fluorescent X-rays obtained from an object to be measured. A device function of the detection system is obtained for each analytic element, based on the energy resolution of the detection system for a fluorescent X-ray energy value of each analytic element. A deconvolution process is effected on the measured waveform thus smoothed, by using the device functions of the detection system. Analytic elements are identified and concentrations of the analytic elements are obtained from the waveform data after the deconvolution process. The measured waveform is compensated for absorption in a beryllium window prior to smoothing.

7 Claims, 6 Drawing Sheets

FIG. 5A  MEASURED WAVE FORM

FIG. 5B  SMOOTHED WAVE FROM

FIG. 5C  DECONVOLUTED WAVE FORM

FIG. 6

ELEMENT ANALYZING METHOD

BACKGROUND OF THE INVENTION

1. Field of the Invention

The present invention relates to an element analyzing method using fluorescent X-rays, and more particularly to an element analyzing method which makes possible precise identification of light elements and precise calculation of concentrations thereof.

2. Related Background Art

The X-ray fluorescence analysis has been heretofore used as a nondestructive element analysis for an object to be measured (sample). The total reflection X-ray fluorescence analysis was developed to improve the sensitivity and is under study for applications to contamination control in semiconductor processes. Among the total reflection X-ray fluorescence analyses, the energy dispersive X-ray fluorescence analysis permits measurement of spectrums in a wide range of energy, so that multiple elements can be simultaneously analyzed thereby by using a single solid-state detector (SSD) disposed immediately above the sample. Since the energy dispersive X-ray fluorescence analysis needs no analyzing crystal, the SSD can be set closer to the sample. Therefore, the energy dispersive method has the feature of higher sensitivity for example than the wave dispersive method in X-ray fluorescence analysis.

The energy-dispersive total reflection X-ray fluorescence analysis is inferior in spectrum resolution to the wave length dispersive method, providing a smaller total count number. Also, the total reflection method tends to have impeding peaks, for example escape peaks, peaks due to influence of diffraction beams, sum peaks ($2K_\alpha$; $K_\alpha + K_\beta$), peaks due to the Compton scattering, and so on.

The conventional energy dispersive X-ray fluorescence analysis permits easy discrimination between element peaks and impeding peaks if concentrations of contaminating elements are high. It is, however, difficult to discriminate light elements in concentrations of not more than $10^9$ atoms/cm$^2$, which is required in semiconductor processes, by using the conventional energy dispersive method. Reasons for this difficulty are as follows.

(1) The generation probability (fluorescence yield) of the $K_\alpha$ spectrum is for example 0.02 for Na, which is 1/20 of 0.4 for Zn. Thus, even if light elements (Na to Cl) exist in a sample in the same concentration as heavy elements, a total count number ($K_\alpha$ fluorescent line) obtained for each light element is smaller than those for heavy elements.

(2) A beryllium (Be) window is set at the fore end of the solid-state detector to maintain a high vacuum inside the detector and to prevent contamination on the surface of a Si crystal, of which the solid-state detector is made. The Be window absorbs the $K_\alpha$ spectrum. That is, if the Be window has a thickness of about 10 μm, a light element lighter than F cannot be detected because of the absorption of the $K_{60}$ line. Elements above Cl are free of the influence of absorption of the $K_\alpha$ line. Further, elements between F and Cl are influenced by the absorption depending upon the mass absorption coefficient thereof.

(3) Since a sample is made mainly of Si in a semiconductor process, the resultant spectrum will include peaks of Na to Cl elements on the tail of the $K_\alpha$ spectrum of the Si element. Thus, some means is required for making the half width of the Si peak as narrow as possible, for example, means for setting the X-ray incident angle amply smaller than the critical angle. This technique, however, decreases the total count number obtained, resulting in being readily affected by statistical error of counting.

SUMMARY OF THE INVENTION

The present invention has been accomplished by taking the above points into consideration. It is an object of the present invention to provide an element analyzing method which permits precise identification of analytic elements, particularly light elements, and precise calculation of the concentrations thereof.

An element analyzing method according to the present invention comprises the steps of:

smoothing a measured waveform of fluorescent X-rays obtained from an object to be measured;

obtaining a device function of a detection system for each analytic element, based on an energy resolution of the detection system to a fluorescent X-ray energy value of said each analytic element;

performing a deconvolution process using said device functions, for the measured waveform as smoothed; and identifying the analytic elements and obtaining concentrations thereof from the measured waveform after the deconvolution process.

An element analyzing method according to the present invention comprises steps of:

smoothing a measured waveform of fluorescent X-rays obtained from an object to be measured;

obtaining a device function of a detection system for each analytic element, based on an energy resolution of the detection system to a fluorescent X-ray energy value of said each analytic element;

performing a deconvolution process using said device functions, for the measured waveform as smoothed; and identifying the analytic elements from the measured waveform after the deconvolution process.

The present invention is effective in correcting waveform distortion caused by the energy resolution of the detection system by the deconvolution process using the device functions of the detection system.

DESCRIPTION OF THE PREFERRED EMBODIMENTS

Embodiments of the present invention will be described in detail with reference to the accompanying drawings.

First Embodiment

Figure 1:
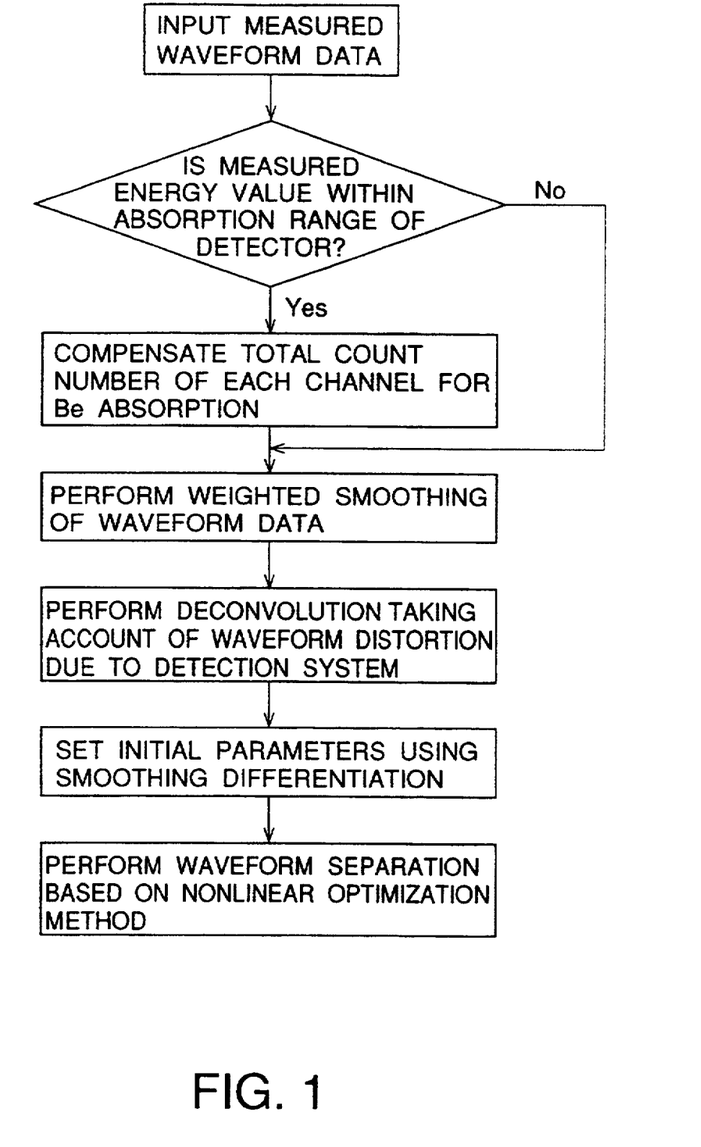
FIG. 1 is a flowchart indicating a first embodiment of element analyzing method according to the present invention.
Figure 2:
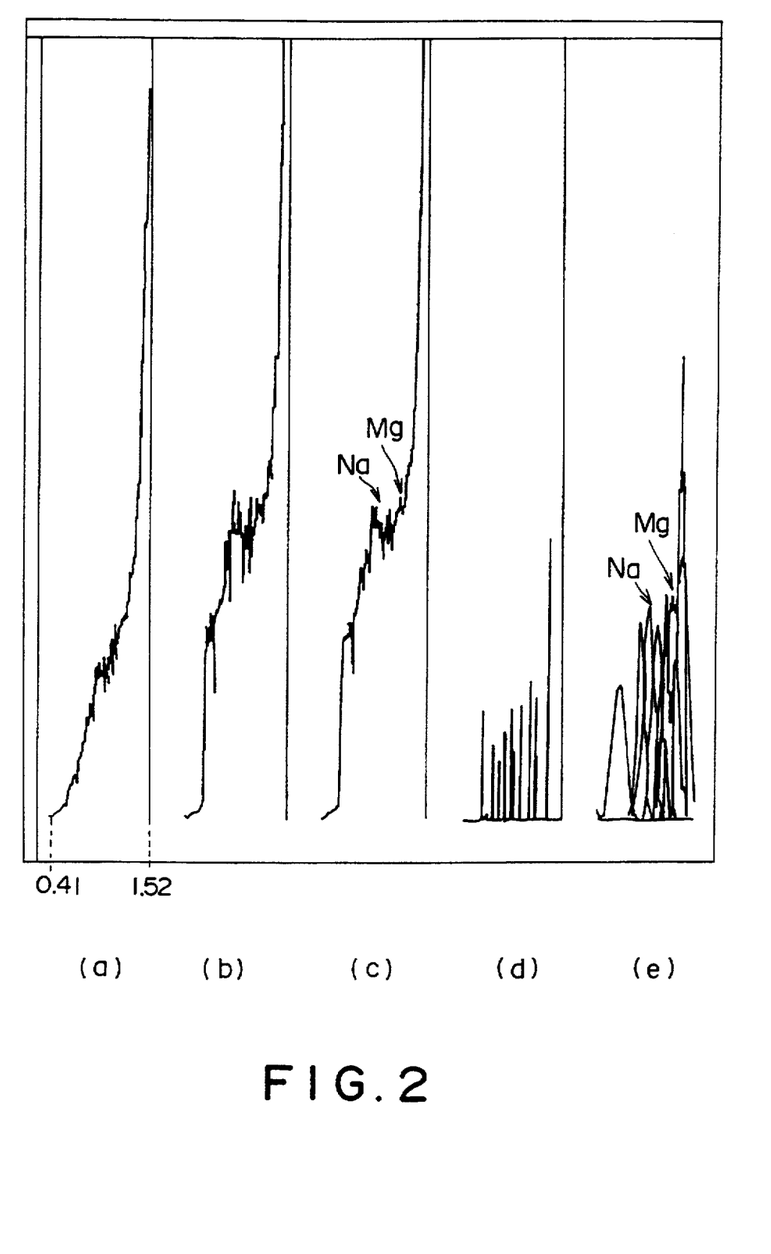
FIG. 2 is a graph showing a specific example of the first embodiment.
Figure 3:
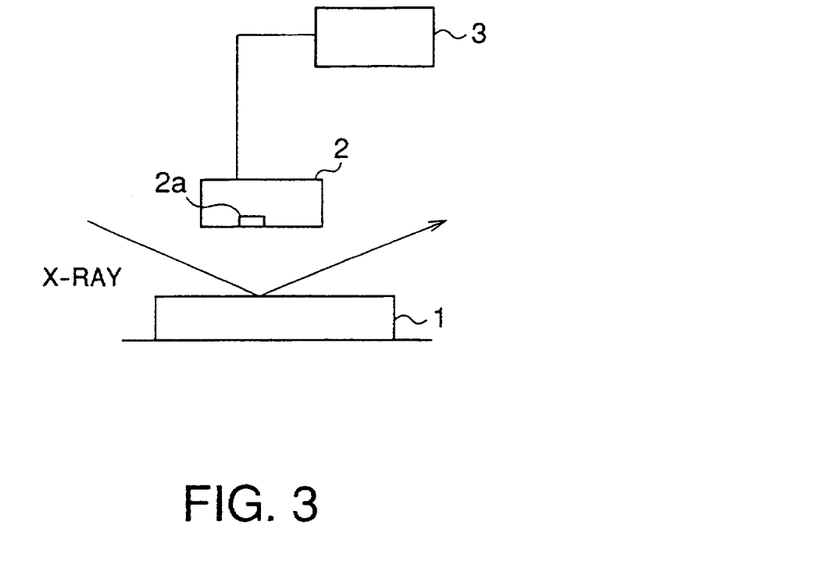
FIG. 3 is a schematic diagram showing an energy dispersive X-ray fluorescence analyzing apparatus.

FIG. 1 to FIG. 3 indicate a first embodiment of element analyzing method according to the present invention.

In FIG. 3, an X-ray beam irradiates a sample 1 (an object to be measured) such as a semiconductor wafer made of Si, and fluorescent X-rays generated from the sample 1 are detected by a solid-state detector 2 (SSD). Connected to the solid-state detector 2 is a signal processing unit 3, which processes electric signals output from the solid-state detector 2. A beryllium (Be) window 2a (with thickness of about 10 $\mu$m) is set at the fore end of the solid-state detector 2. Further, the signal processing unit 3 includes a FET, preamp, A-D converter, and other elements.

Next, with reference to FIG. 1 to FIG. 3, a contaminating-element analyzing method using the energy dispersive X-ray fluorescence analyzing apparatus will be described.

The X-ray beam is first radiated to impinge on the sample 1 containing contaminating elements, and the solid-state detector 2 detects fluorescent X-rays from the sample 1. A waveform of the fluorescent X-rays thus measured is then input into the signal processing unit 3.

The signal processing unit 3 performs the following signal processing for the measured waveform of the fluorescent X-rays. In the input data of the measured waveform, absorption takes place in the Be window in the fluorescent X-ray energy range of light elements. For example with a Be window of a thickness of about 10 $\mu$m, 100% of the fluorescent X-ray energy is absorbed at the energy value of 0.55 keV while 0% of the fluorescent X-ray energy is absorbed at the energy value of 2.5 keV. That is, the following relation holds.

$$I/I_0 = \exp\{-(\mu/\rho)\cdot\rho\cdot Z\} \tag{1}$$

In the above equation $I/I_0$ represents an absorption coefficient, $\mu/\rho$ a mass absorption coefficient of Be, $\mu$ the density of Be (1.85 g/cm$^3$), and Z the thickness of Be window (which is assumed to be 10 $\mu$m in calculation).

As shown in FIG. 1, a count (Ci) in each channel within the energy range of from 0.55 keV to 2.5 keV in the initially input data of the measured waveform is multiplied by the reciprocal of the absorption coefficient $I/I_0$ (Ai) as described above, to obtain a count value (Ci') of the fluorescent X-rays which is originally to pass through the Be window.

$$Ci' = Ai^{-1} \times Ci \tag{2}$$

(where i represents a channel number).

A 5-point weighted smoothing process is carried out for the measured waveform thus corrected mainly to reduce background noises.

An improvement process (deconvolution process) is next carried out to improve waveform distortion in the detection system composed of SSD, FET, preamp and A-D converter. The SSD has the energy resolution of about 100 eV for energy value of 2 keV and about 150 eV for energy value of 6 keV.

Then a device function of the detection system is prepared for each analytic element, based on the energy resolution of the detection system for the fluorescent X-ray energy value of each analytic element. Using the device functions, the deconvolution process is effected on the measured waveform after the smoothing process.

A device function of the detection system can be expressed by a Gaussian function G (X) having a half width of the energy resolution.

$$G(X) = \frac{\sqrt{\ln 2}}{Wh\sqrt{\pi}} \cdot \exp\left(-\ln 2 \times \frac{X^2}{Wh^2}\right) \tag{3}$$

$$Wh = \sqrt{C_N^2} + C \cdot E \tag{4}$$

In the above equations, X represents a channel number, Wh a half width of energy corresponding to $K_\alpha$ spectrum value of each element, $C_N$ a noise component, C a constant, and E an energy value of the fluorescent X-ray spectrum of each element.

The deconvolution process is carried out by using the Gaussian functions as device functions for the measured waveform as so smoothed. Specifically, values of E are set as 6.398 keV, 7.471 keV and 8.630 keV for analytic elements to be measured of Fe, Ni, and Zn in the measured waveform, and then device functions are obtained for the elements by Equations (3) and (4). The deconvolution process is done for each measured waveform within ±500 eV around each spectrum value. The actual calculation of the deconvolution process is carried out by using the Gauss-Seidel method.

That is, if the actual waveform data of the fluorescent X-rays is I, and the waveform data measured through the model function G (X) is O, the following relation is obtained.

$$O = I \times G(X) \tag{5}$$

Then the actual waveform data I is obtained by the following equation.

$$I = \overline{O}/G(X) \tag{6}$$

After the deconvolution process, differential smoothing is carried out for the measured waveform. The smoothing is done with seven points, taking into consideration the width of the energy band and the energy resolution of each channel (each point on the horizontal axis in the measured waveform). Zero points are next detected from the differentiated waveform as candidates of peaks in the measured waveform.

Then a model function, for example a Gaussian function, is prepared for each peak in the measured waveform, and a model waveform is constituted by a linear sum of the Gaussian functions. In this case, each Gaussian function has initial parameters of peak energy position u, peak height h and half value of half maximum w, which are variables in each Gaussian function.

The model waveform is expressed by the following equation.

$$z(i, p) = \Sigma j h \cdot \exp\{-\ln 2(\nu - u)^2/w^2\}$$

(where j corresponds to each peak detected).

The peak energy position u in each Gaussian function can be approximately determined from the channel number i corresponding to each peak in the waveform data. Also, the peak height h can be approximately determined from each peak in the waveform data. Further, the half width at half maximum w can be approximately determined on the basis of a point where the third differential of the function becomes 0.

A nonlinear optimization process is next carried out to minimize the residual sum of squares between the measured waveform and the model waveform constituted by the linear sum of Gaussian functions prepared for the peaks in the measured waveform, whereby the aforementioned initial parameters are determined and separated waveforms of Gaussian functions are obtained. In more detail, an objective function e (p) is defined as follows to stand for the residual sum of squares between the model waveform z (i, p) and the measured waveform y (i):

$$e(p) = \Sigma \{z(i, p) - y(i)\}^2,$$

where $$z(i, p) = \Sigma_j h \cdot \exp\{-\ln 2(v-u)^2/w^2\}$$

(where j corresponds to each peak detected).

The vector variable p to minimize this objective function e (p) is obtained by using the nonlinear optimization method based on the simplex method. It should be noted that another technique (for example the DFP method) can be used in place of the simplex method.

Then the energy positions of separated waveforms are compared one by one with the $K_\alpha$ radiation peak positions of respective elements, based on the separated waveforms of Gaussian functions obtained by the nonlinear optimization process. The comparison is done with a certain margin taking a chemical shift into consideration. If a Gaussian function is found to correspond to a $K_\alpha$ radiation peak position of an element, the Gaussian function is identified to stand for the element (contaminating element). Peaks having no corresponding elements are identified as escape peaks, sum peaks or background noises. Next obtained is an integrated intensity (area) of each Gaussian function for a corresponding element. In this case, each Gaussian function is integrated in the range of $\pm 4$ w, where w represents the half width at half maximum of the Gaussian function.

Specific Example

A specific example of the first embodiment will next be described referring to FIG. 2. FIG. 2 shows in (a) data of measured waveform initially obtained in the energy range of 0.41 to 1.52 keV. FIG. 2 (b) shows data of measured waveform which was corrected using the absorption coefficients, for waveform distortion of light elements caused by the absorption in the Be window. Further, FIG. 2 (c) shows data of measured waveform after the 5-point weighted smoothing process. Also, FIG. 2 (d) shows data of measured waveform after the deconvolution process using the device functions for correcting the waveform distortion caused by the energy resolution of the detection system. FIG. 2 (e) shows data of measured waveform after peak separation based on the nonlinear optimization process.

It is seen from FIG. 2 that it is difficult to discriminate peaks of Na and Mg in the original measured waveform data (shown in FIG. 2 (a)) while the peaks of the light elements can be discriminated in the separated waveform data after the waveform distortion correction in the present invention.

As described above, the present embodiment is effective for identifying the light elements and for calculating the concentrations thereof with precision by correcting the waveform distortion due to the absorption in the Be window in SSD, which is seen particularly with the light elements, and the waveform distortion caused by the energy resolution of the detection system.

In the case where hydrocarbon contamination is deposited on the Be window, or in the case where an ice film is formed on the Si crystal surface of the solid-state detector upon cooling, the sensitivity of Na-$K_\alpha$ spectrum can be lowered, or the detection sensitivity can be lowered in the region of light elements. In such cases, the present invention is very effective for waveform distortion correction in the region of light elements.

Second Embodiment

A second embodiment of element analyzing method according to the present invention will be described referring to FIG. 4 to FIG. 6.

An X-ray beam first irradiates a blank sample. A 5-point weighted smoothing process is carried out for a measured waveform of the blank sample input into the processing unit to reduce the background noises. Then the X-ray beam irradiates a sample containing contaminating elements to obtain a measured waveform of fluorescent X-rays. The measured waveform is compensated for the absorption of fluorescent X-rays from the light elements in the Be window and thereafter the smoothing process is carried out. Then a device function of the detection system is prepared for each analytic element on the basis of the energy resolution of the detection system for a fluorescent X-ray energy value of the each analytic element. The deconvolution process is effected on the smoothed, measured waveform by using the device functions.

The smoothing process and the deconvolution process are the same as those in the first embodiment, and therefore description thereof will not be repeated.

The same point on the blank sample is consecutively measured ten times to obtain a variation range of channel number for a spectrum corresponding to each element. This variation range is obtained as a detection error caused by the detection system.

Figure 4:
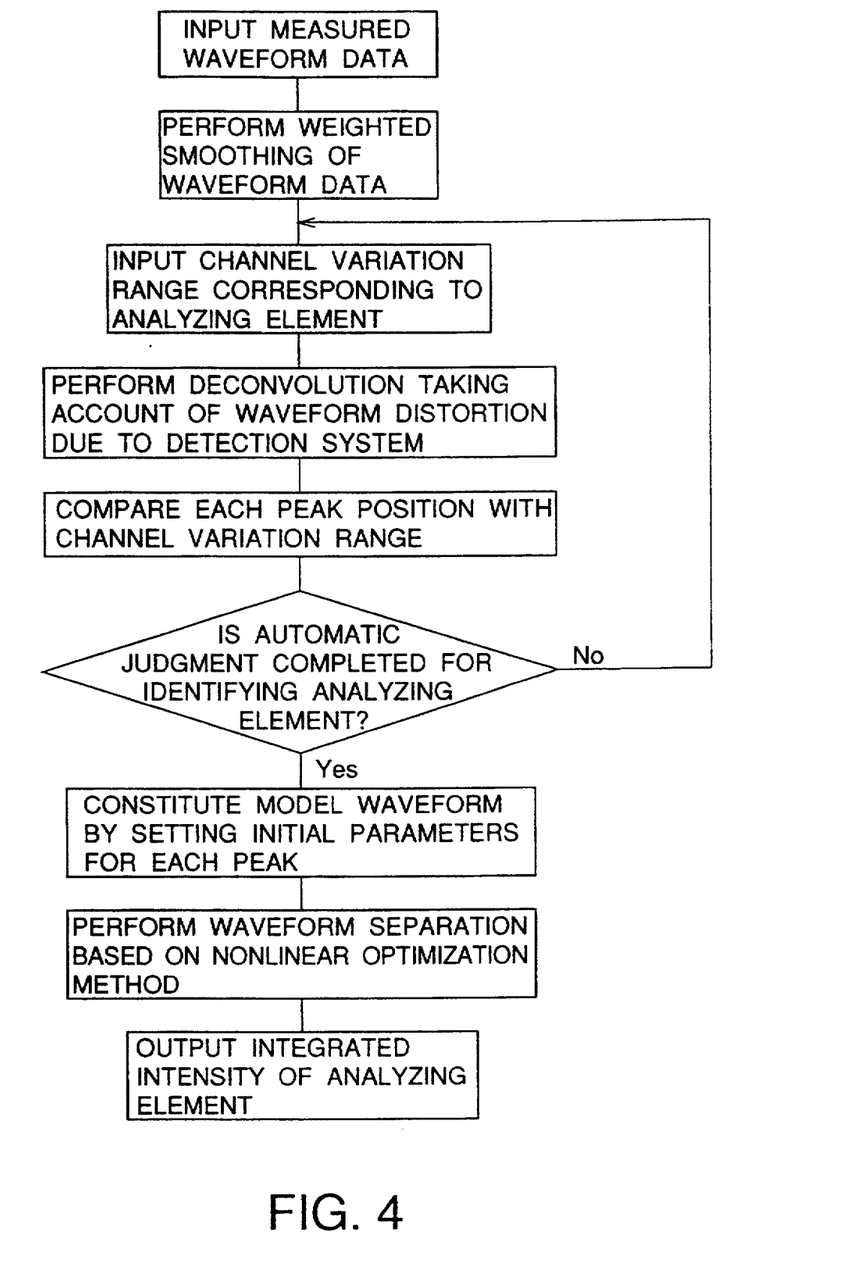
FIG. 4 is a flowchart indicating a second embodiment of element analyzing method according to the present invention.

An actual sample is processed according to the flowchart shown in FIG. 4. After a measured waveform is obtained, the smoothing process (5-point weighted averaging process) is carried out over the entire range. Next input are the channel variation ranges preliminarily obtained for the analytic elements with the blank sample.

A device function for the deconvolution process is next determined for each objective analytic element. Then the deconvolution process is carried out by using the device functions for the measured waveform within $\pm 500$ eV around the energy value of $K_\alpha$ spectrum of each objective analytic element.

If in the waveform data there is a peak within the variation range of the channel number preliminarily obtained with the blank sample in identifying the objective analytic elements in the measured waveform after the deconvolution process, it is automatically judged that the identification of the objective analytic element is completed.

If concentrations of the elements are further calculated from the identified peaks, a model waveform is constituted by a linear sum of Gaussian functions prepared for the peaks in the measured waveform. The nonlinear optimization process is conducted to minimize the residual sum of squares between the measured waveform after the deconvolution process and the model waveform, whereby the initial parameters in each Gaussian function are obtained and separated waveforms of the Gaussian functions are obtained. An integrated intensity is then calculated for each Gaussian function. As described above, the element identification and the concentration calculation are automatically processed.

Specific Example

A specific example of the second embodiment will be next described referring to FIGS. 5A–5C and FIG. 6.

Figure 5A:
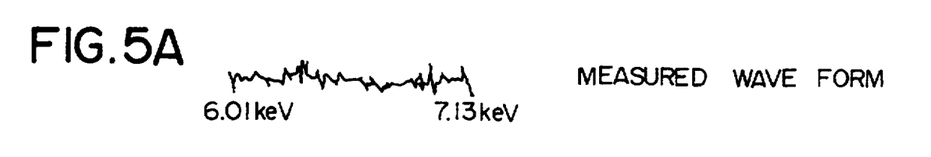
FIG. 5A is a graph showing a measured waveform in a specific example of the second embodiment.
Figure 5B:
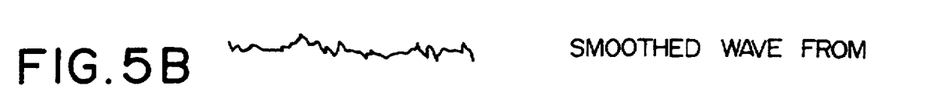
FIG. 5B is a graph showing a smoothed waveform in the second embodiment.
Figure 5C:
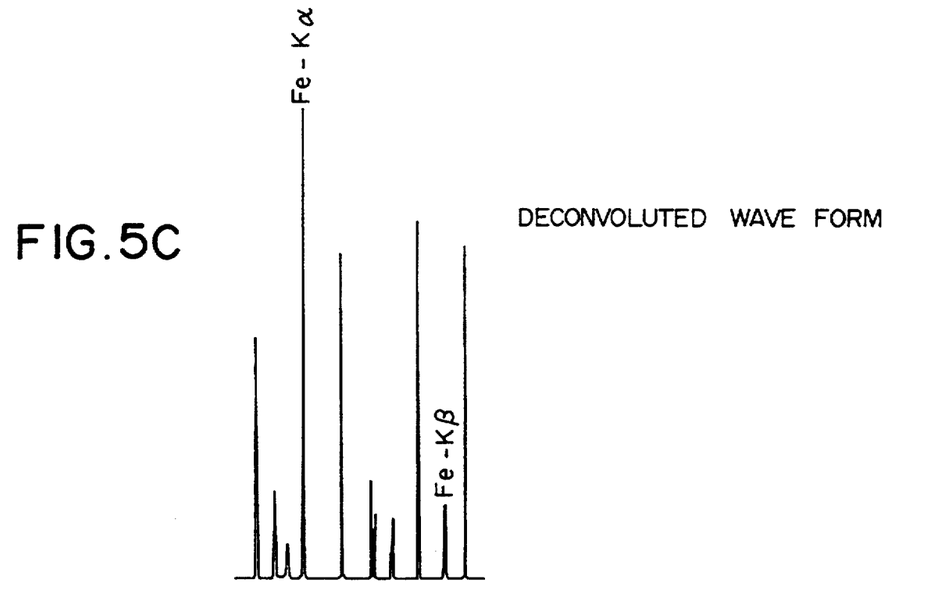
FIG. 5C is a graph showing a deconvoluted waveform in the second embodiment.

FIG. 5A shows a measured waveform initially obtained, FIG. 5B the measured waveform after the 5-point weighted smoothing process, and FIG. 5C data of the measured waveform after the deconvolution process. In FIGS. 5A–5C, the energy range is from 6.01 to 7.13 keV, in which a peak of Fe-$K_\alpha$ is located at the energy position of 6.398 keV and a peak of Fe-$K_\alpha$ at the energy position of 7.057 keV. The total count number is 0–15 (cts) for any channel in the measured waveform initially obtained (as shown in FIG. 5A), while the count number is about 200 (cts) for the channel corresponding to Fe-$K_\alpha$ in the measured waveform after the deconvolution process (as shown in FIG. 5C).

As shown in FIGS. 5A–5C, the method can clearly identify existence of even a peak from a contaminating element in low concentration of the order of $10^9$ atoms/$cm^2$.

It was found that the channel variation range was ±3 channels in ten consecutive measurements at the same point on the blank sample with the 5-point weighted smoothing process and the deconvolution process. This change corresponds to a fluctuation error caused by the apparatus.

Figure 6:
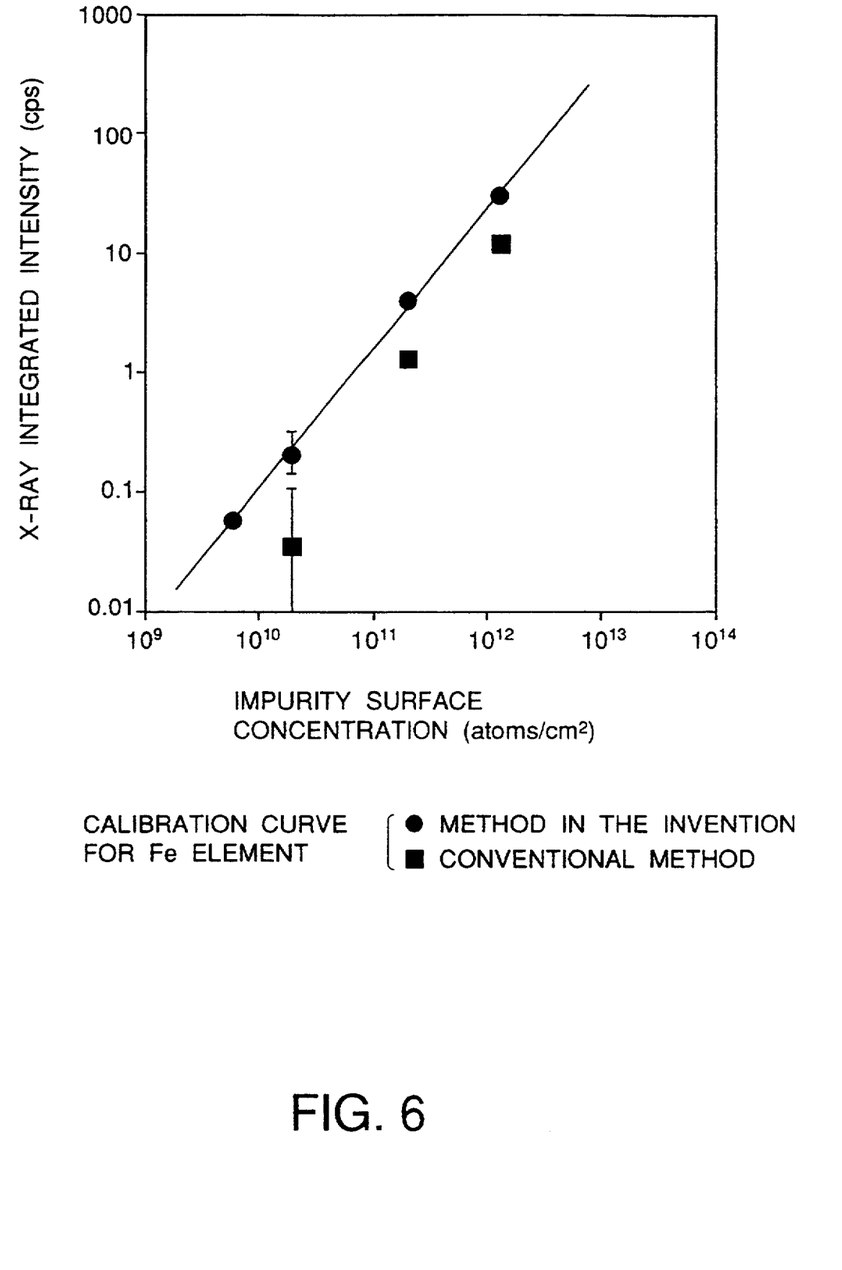
FIG. 6 is a graph showing a calibration curve of Fe element to illustrate a specific example of the second embodiment.

FIG. 6 shows integrated intensities of a specific element (Fe) calculated from data of measured waveform after the deconvolution process and the nonlinear optimization process. As shown in FIG. 6, the concentrations can be detected with precision by performing the deconvolution process in the present invention as compared with the conventional method without performing the deconvolution process.

As detailed above, the present invention is effective for correcting the waveform distortion caused by the energy resolution of the detection system by the deconvolution process using the device functions of the detection system. Therefore, the element identification and the concentration calculation can be done with precision.

What is claimed is:

1. An element analyzing method comprising the steps of:
    smoothing a measured waveform of fluorescent X-rays obtained from an object to be measured;
    obtaining a device function of a detection system for each analytic element, based on an energy resolution of the detection system to a fluorescent X-ray energy value of said each analytic element;
    performing a deconvolution process using said device functions, for the measured waveform thus smoothed; and
    identifying the analytic elements and obtaining concentrations thereof from the measured waveform after the deconvolution process.

2. An element analyzing method according to claim 1, wherein said measured waveform of the fluorescent X-rays is obtained after the fluorescent X-rays generated from the object to be measured passes through a beryllium window in a solid-state detector.

3. An element analyzing method according to claim 2, wherein prior to the step of smoothing, a further step is added for compensating the measured waveform of the fluorescent X-rays from the object to be measured for absorption of the fluorescent X-rays in the beryllium window in the solid-state detector.

4. An element analyzing method according to claim 1, wherein said step of identifying the analytic elements and obtaining concentrations thereof comprises the steps of:
    performing a differential smoothing process with respect to the measured waveform to detect peaks therein;
    preparing a model function with an initial parameter as a variable for each peak in the measured waveform, and constituting a model waveform by a linear sum of the model functions;
    performing a nonlinear optimization process so as to minimize a residual sum of squares between the model waveform and the measured waveform thereby to determine the initial parameter in each model function, thereby obtaining separated waveforms; and
    identifying contaminating elements respectively corresponding to the separated waveforms, based thereon, and obtaining an integrated intensity of separate waveform for each contaminating element as identified.

5. An element analyzing method comprising the steps of:
    smoothing a measured waveform of fluorescent X-rays obtained from an object to be measured;
    obtaining a device function of a detection system for each analytic element, based on an energy resolution of the detection system to a fluorescent X-ray energy value of said each analytic element;
    performing a deconvolution process by using said device functions, for the measured waveform thus smoothed; and
    identifying the analytic elements from the measured waveform after the deconvolution process.

6. An element analyzing method according to claim 5, wherein said step of identifying the analytic elements comprises the steps of:
    smoothing a plurality of measured waveforms of fluorescent X-rays obtained from a blank material containing no contaminating element;
    obtaining a range of change of channel number for each spectrum corresponding to an element, based on the plurality of measured waveforms of the blank material; and
    identifying the analytic elements by whether each peak of a measured waveform after the deconvolution process is within the range of change of channel number obtained from the blank material.

7. An element analyzing method according to claim 5, further comprising a step of obtaining concentrations of the analytic elements after the step of identifying them,
    wherein said step of obtaining concentrations of the analytic elements comprises the steps of:
    performing a differential smoothing process for the measured waveform to detect peaks therein;

preparing a model function with an initial parameter as a variable for each peak in the measured waveform, and constituting a model waveform by a linear sum of the model functions;

performing a nonlinear optimization process so as to minimize a residual sum of squares between the model waveform and the measured waveform, so as to determine the initial parameter in each model function, thereby obtaining separated waveforms; and obtaining an integrated intensity of a separate waveform for each contaminating element as identified, based on the separated waveforms.

* * * * *